US00PP29284P3

(12) United States Plant Patent
Layt

(10) Patent No.: US PP29,284 P3
(45) Date of Patent: May 8, 2018

(54) *ZOYSIA* PLANT NAMED 'LSA01'

(50) Latin Name: *Zoysia macrantha*
Varietal Denomination: LSA01

(71) Applicant: Todd Anthony Layt, Clarendon (AU)

(72) Inventor: Todd Anthony Layt, Clarendon (AU)

( * ) Notice: Subject to any disclaimer, the term of this patent is extended or adjusted under 35 U.S.C. 154(b) by 33 days.

(21) Appl. No.: 15/330,896

(22) Filed: Nov. 10, 2016

(65) Prior Publication Data

US 2017/0142889 P1 May 18, 2017

(30) Foreign Application Priority Data

Nov. 15, 2015 (AU) ..... PBR 2015/311

(51) Int. Cl.
*A01H 5/12* (2018.01)

(52) U.S. Cl.
USPC ..... Plt./390

(58) Field of Classification Search
USPC ..... Plt./390
See application file for complete search history.

*Primary Examiner* — Keith O Robinson
(74) *Attorney, Agent, or Firm* — Samuel R. McCoy, Jr.

(57) ABSTRACT

A new and distinct cultivar of *Zoysia macrantha* plant named 'LSA01', characterized by the combination of a fast rate of growth, freely branched stolons, medium leaf blade and good salt tolerance. The new variety propagates successfully by stolon and rhizome division and has shown to be uniform and stable in the resulting generations from asexual propagation.

3 Drawing Sheets

Latin name of the genus and species: The Latin name of the genus and species of the novel variety disclosed herein is *Zoysia macrantha*.

Variety denomination: The novel variety of *Zoysia macrantha* disclosed herein has been given the variety denomination 'LSA01'.

BACKGROUND OF THE INVENTION

The present invention relates to a new and distinct perennial variety of *Zoysia macrantha*, which has been given the variety denomination of 'LSA01'. Its market class is that of a turf grass. 'LSA01' is intended for use as a lawn grass in gardening, landscaping, sports fields and amenity horticulture.

Parentage: The new cultivar is a seedling selection believed to be the result of the open cross pollination of *Zoysia macrantha* 'MAC03' (U.S. Plant Pat. No. 21,789) with a proprietary *Zoysia macrantha* breeding line identified as "Breeding Line A", developed and owned by the same inventor. During the 2012 growing season, a small population of pot-grown 'MAC03' and Breeding Line A plants were grown in close proximity to facilitate cross pollination. Later in the same growing season, seed was collected from both populations and subsequently sown into nursery pots. These seedlings were then grown to a mature age for evaluation. In 2013, one seedling was observed which exhibited a faster rate of growth and more freely branched stolons. The new cultivar was given the variety denomination, 'LSA01'. The selection process was conducted at the inventor's breeding facility in Clarendon, New South Wales, Australia.

Asexual Reproduction: 'LSA01' was first asexually propagated by cutting and division of stolons and rhizomes in 2012 in Clarendon, New South Wales, Australia. 'LSA01' has since been further asexually propagated by means of cutting and division of stolons and rhizomes through five generations. The distinctive characteristics of the variety have remained stable and true to type through successive cycles of asexual propagation.

SUMMARY OF THE INVENTION

The cultivar 'LSA01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'LSA01'. These characteristics in combination distinguish 'LSA01' as a new and distinct *Zoysia* cultivar:

1. *Zoysia* 'LSA01' exhibits a fast rate of growth; and
2. *Zoysia* 'LSA01' exhibits freely branched stolons; and
3. *Zoysia* 'LSA01' exhibits good tolerance to salt; and
4. *Zoysia* 'LSA01' exhibits a medium leaf width; and
5. Long stolon length.

BRIEF DESCRIPTION OF THE PHOTOGRAPHS

DETAILED BOTANICAL DESCRIPTION

Figure 1:
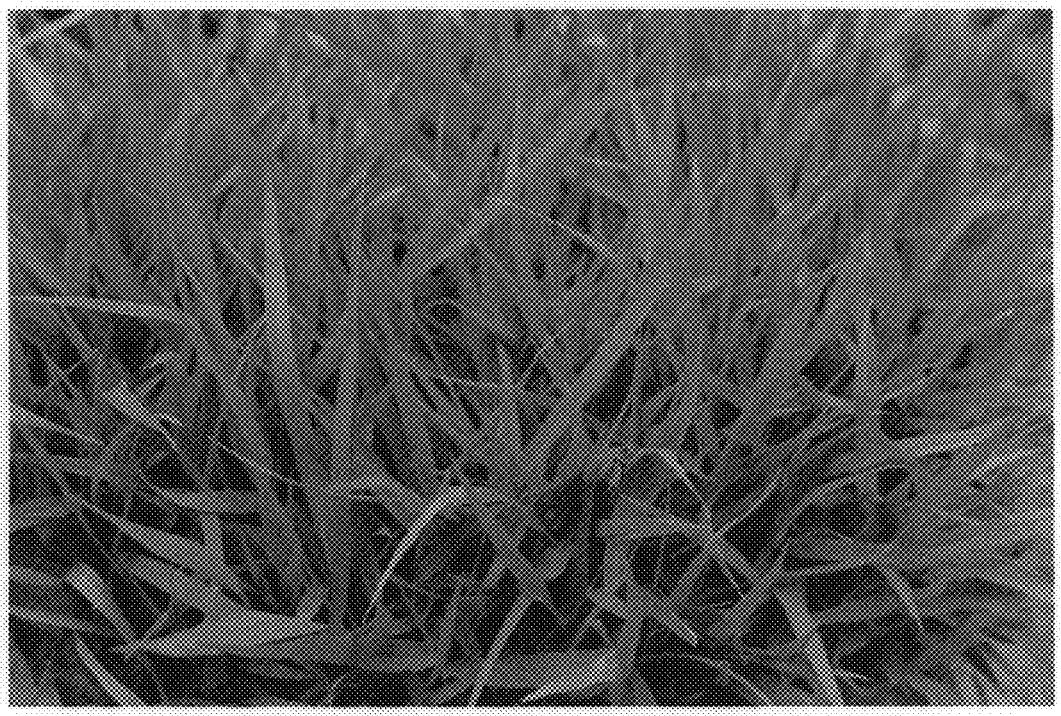
FIG. 1 illustrates, as nearly true as it is reasonably possible to make the same in color illustrations of this type, the mature sward of a 12 month-old 'LSA01' plant grown in a 200 mm nursery pot. Colors in the photographs differ slightly from the color values cited in the detailed description, which accurately describes the colors of 'LSA01'.
Figure 2:
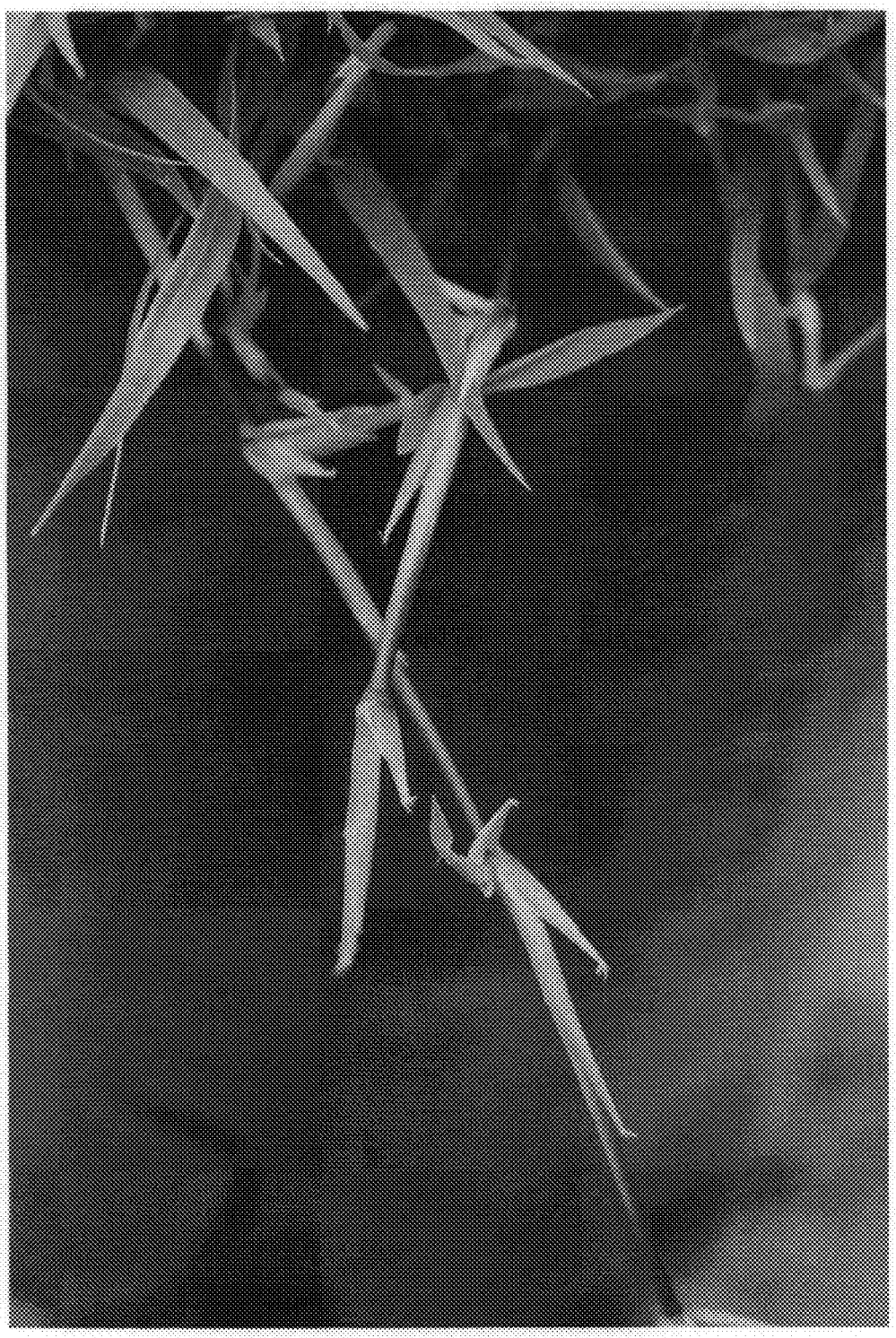
FIG. 2 illustrates, as nearly true as it is reasonably possible to make the same in color illustrations of this type, an exemplary stolon of 'LSA01' of a 12 month-old 'LSA01' plant grown in a 200 mm nursery pot.
Figure 3:
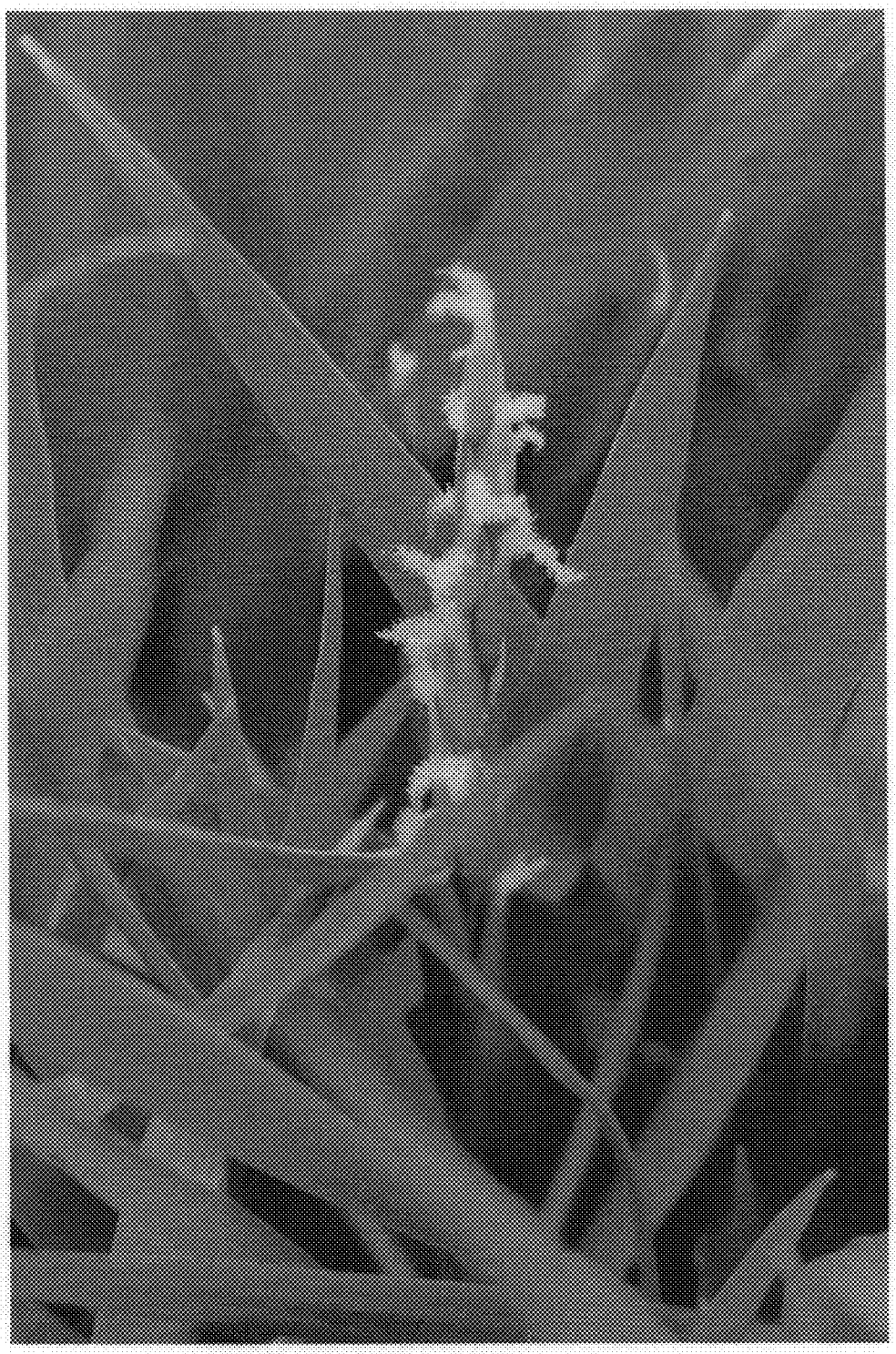
FIG. 3 illustrates, as nearly true as it is reasonably possible to make the same in color illustrations of this type, an exemplary inflorescence of 'LSA01' of a 12 month-old 'LSA01' plant grown in a 200 mm nursery pot.

The following is a detailed botanical description of a new and distinct variety of a *Zoysia macrantha* turf grass plant known as 'LSA01'. Unless indicated otherwise, the descriptions disclosed herein are based upon observations made in October of 2016 of 12 month old 'LSA01' plants grown in 200 mm nursery pots in Clarendon, New South Wales, Australia. Plants were grown in full sun and maintained using regular overhead irrigation. Only one application of slow-release fertilizer was applied to the plants and no pest or disease measures were taken. Plants were untrimmed.

Those skilled in the art will appreciate that certain characteristics will vary with older or, conversely, with younger plants. 'LSA01' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2003 edition.

A botanical description of 'LSA01' and comparisons with the parent plants and closest known cultivar of *Zoysia macrantha* are provided below.

Plant description:

*Growth habit.*—Perennial plant with a prostrate growth habit forming a tight mat of stolons which root adventitiously on the ground surface and branch heavily at the stolon nodes. Culms are prostrate, becoming decumbent when flowering.

*Growth rate.*—Very vigorous.

*Disease and pest tolerance or resistance.*—Neither tolerance nor resistance to normal diseases and pests of *Zoysia macrantha* has been observed.

*Temperature tolerance.*—*Zoysia macrantha* is known to tolerate temperatures from approximately 10 degrees F. to at least 115 degrees F.

*Drought tolerance.*—Like other *Zoysia* species, 'LSA01' exhibits good drought tolerance relative to other Genus of warm season grasses such as *Stenotaphrum* sp.

*Soil tolerances.*—Tolerant of most soil types; from sandy loam to loamy clay; maintains good turf quality in low-fertility soils.

*Propagation.*—Typical time to develop roots is similar to that of other *Zoysia* grasses; approximately 2 to 4 weeks. Average crop time to produce an initial mature and marketable stand of turf grass sod is approximately 7 to 9 months. Precise timing varies depending on fertilizer and water inputs as well as geographical location.

Root system: Root system is typical for that of *Zoysia* grass species; a network of rhizomes and fibrous feeder roots. Rhizomes are colored orange-white, nearest to RHS 159D.

Stolons:

*Stolon length.*—The mean length is approximately 80 mm.

*Stolon width.*—Mean width is approximately 1 mm.

*Stolon color.*—Exposed surfaces are yellow-green, RHS 144A; unexposed surfaces are purple, RHS N77A.

*Stolon internode color.*—Exposed surfaces are greyed-purple, RHS 187A; unexposed surfaces are yellow-green, RHS 144A.

*Stolon internode length.*—10 to 20 mm on mature stolons.

Culms:

*Culm attitude.*—Prostrate; semi-decumbent when flowering.

*Culm length.*—Mean length is 75 mm, from stolon node to apex above.

*Culm internode length.*—10 to 20 mm.

*Color.*—Green, RHS 138A.

Foliage:

*Attachment.*—Cauline.

*Length of blade.*—Mean length is 75 mm; flag leaf on flowering culm has a mean length of 125 mm.

*Width of blade.*—Mean width is 4 mm; flag leaf is 4 mm wide.

*Shape of blade.*—Linear.

*Leaf shape; apex.*—Acute.

*Leaf aspect.*—Concave.

*Margin.*—Entire; ciliate.

*Texture* (*adaxial & abaxial surfaces*).—Smooth.

*Hairiness* (*adaxial & abaxial surfaces*).—Glabrous.

*Juvenile leaf color* (*adaxial surface*).—Green, RHS 137B.

*Juvenile leaf color* (*abaxial surface*).—Green, RHS 137B.

*Mature leaf color* (*adaxial surface*).—Green, RHS 137B.

*Mature leaf color* (*abaxial surface*).—Green, RHS 137B.

*Venation.*—Parallel.

*Venation color.*—All veins are colored the same of surrounding leaf surface; all veins are green, RHS 137B.

*Leaf sheath.*—Glabrous, ranging from 8 to 10 mm long. Color approximates to yellow-green, RHS 145A.

*Collar.*—Approximately 1 mm, and constricted. Color approximates to yellow-green, RHS 146C.

*Ligule.*—A fringe of approximately 10 to 15 hairs, ranging in length from 1 to 3 mm.

Inflorescence and flower:

*Natural flowering season.*—Spring to fall; in Northern hemisphere, April to November.

*Inflorescence type and habit.*—Terminal spike-like raceme, comprised of eight alternate pairs of appressed spikelets.

*Total inflorescence size.*—Approximately 25 mm long by 1 mm wide.

*Rachilla.*—Curved; approximately 2 mm in length; width is approximately 0.25 mm; color is yellow-green, nearest to RHS 146A.

*Color of spikelets.*—The immature lemmas are yellow-green, RHS 146A, and mature to a greyed-purple corresponding to RHS 183B.

*Shape of spikelets.*—Narrowly ovoid with an acute apex.

*Dimensions of spikelets.*—Approximately 2 mm long and less than 1 mm wide.

*Glumes.*—Approximately 2 mm long and less than 1 mm wide; color is yellow-green, RHS 146A.

*Lemma.*—Approximately 1.5 mm long and less than 0.5 mm wide; predominant color is yellow-green, nearest to RHS 144D, with a darker stripe, nearest to RHS 146A.

*Awns.*—Absent.

Reproductive organs:

*Androecium.*—Not observed.

*Gynoecium.*—Style — Approximately 1 mm long and 0.1 mm wide. Stigma — Featherlike; length is approximately 1 mm; wide is approximately 0.5 mm; color is white, nearest to RHS N155A. Ovary — Not observed.

Seeds and fruits: The number of seed per raceme, seed dimensions and color of seed correspond to the number of spikelets, spikelet dimensions and spike color.

COMPARISON WITH THE PARENT PLANTS AND COMMERCIAL COMPARATOR

Plants of the new cultivar 'LSA01' are similar to the parent and only known commercial comparator, *Zoysia macrantha* 'MAC03', in most horticultural characteristics. However 'LSA01' differs from the parent in the following characteristics:

1. The stolons of 'LSA01' are freely branched whereas 'MAC03' exhibits less stolon branching.
2. The stolons of 'LSA01' have a smaller diameter than the stolons of 'MAC03'.
3. The flowering culms of 'LSA01' are longer and have a smaller diameter than the flowering culms of 'MAC03'.
4. The flowering culms of 'LSA01' are colored lighter green than the flowering culms of 'MAC03'.
5. The spikelets of 'LSA01' are colored lighter greyed-purple than the spikelets of 'MAC03'.

Plants of the new cultivar 'LSA01' are similar to the parent, *Zoysia macrantha* known as "Breeding Line A", in most horticultural characteristics. However 'LSA01' exhibits fast rate of growth whereas "Breeder Line A" exhibits a slow growth rate.

That which is claimed is:

1. A new and distinct variety of *Zoysia macrantha* plant named 'LSA01', substantially as described and illustrated herein.

* * * * *